United States Patent [19]

Jaeger

[11] Patent Number: 5,585,576
[45] Date of Patent: Dec. 17, 1996

[54] SAMPLER FOR FLUIDIZED PRODUCT

[76] Inventor: Ben E. Jaeger, 50 Hunter La., Yorkville, Ill. 60560

[21] Appl. No.: 428,025

[22] Filed: Apr. 25, 1995

[51] Int. Cl.$^6$ .................................................. G01N 1/20
[52] U.S. Cl. ................................ 73/863.85; 73/863.54; 73/863.83
[58] Field of Search .................... 73/863.85, 863.81, 73/863.82, 863.83, 863.84, 863.86, 863.54, 863.51, 863.52, 863.57, 863.58, 863.53

[56] References Cited

U.S. PATENT DOCUMENTS

| | | | |
|---|---|---|---|
| 3,726,143 | 4/1973 | Enarsson | 73/863.83 |
| 3,764,230 | 10/1973 | Rybicki et al. | 416/134 R |
| 4,024,765 | 5/1977 | Abonnenc | 73/863.83 |
| 4,147,062 | 4/1979 | Jaeger . | |
| 4,262,533 | 4/1981 | Jaeger . | |
| 4,269,064 | 5/1981 | Johnson et al. | 73/863.84 |
| 4,389,906 | 6/1983 | Bartholomay | 73/863.55 |
| 4,433,587 | 2/1984 | Risdal | 73/863.83 X |
| 4,475,410 | 10/1984 | Jaeger | 73/863.84 |
| 4,479,393 | 10/1984 | Shores | 73/863.82 |
| 4,517,053 | 5/1985 | Devine | 102/251 |
| 4,538,472 | 9/1985 | Skarpness | 73/863.55 |
| 4,562,747 | 1/1986 | Jaeger | 73/863.54 |
| 4,587,856 | 5/1986 | Otis | 73/863.51 |
| 4,630,492 | 12/1986 | Goode | 73/863.82 |
| 4,702,114 | 10/1987 | Cabannes | 73/863.85 |
| 4,744,255 | 5/1988 | Jaeger | 73/863.84 |
| 4,761,084 | 8/1988 | Benton et al. | 384/619 |
| 4,918,999 | 4/1990 | Wenshau et al. | 73/863.54 |
| 4,934,200 | 6/1990 | Lantz | 73/863.85 |
| 5,277,073 | 1/1994 | Ruiz et al. | 73/863.85 |

*Primary Examiner*—Thomas P. Noland
*Attorney, Agent, or Firm*—Juettner Pyle Lloyd & Piontek

[57] ABSTRACT

A sampling apparatus is characterized by a housing having a bore communicating at one end with the interior of a vessel containing fluidized product. A plunger assembly in the bore has a sample chamber intermediate its ends and is reciprocated to project the sample chamber out of the bore and into the vessel to receive a sample of product therein, and to then retract the sample chamber from the vessel and into the bore to a sample collection point. Forward and rearward seals on the plunger to opposite sides of the sample chamber always maintain a liquid seal between the one end of the bore and the sample collection point. The rearward seal comprises a shear bearing having a circumferential groove that receives and retains fluidized product in sealing relation to the bore to seal the shear bearing and thereby the plunger assembly to the bore. The product collection point in the bore includes a plurality of passages in the housing that communicate with the bore and are sized to prevent passage therethrough of relatively large product particles. Upon reciprocation of the plunger assembly to project the sample chamber into the vessel, the shear bearing cuts off and conveys back into the vessel any pieces of product that became caught in the passages during the previous sampling cycle and extend into the bore.

16 Claims, 2 Drawing Sheets

SAMPLER FOR FLUIDIZED PRODUCT

BACKGROUND OF THE INVENTION

The present invention relates to apparatus for extracting samples of product from flow lines or tanks, and in particular to an apparatus for extracting samples of a fluidized product, such as wood pulp, from a flow line or tank.

Certain manufacturing operations require that the immediate or average composition of a product flowing through a pipe or within a vessel be monitored. This is usually accomplished with apparatus known as samplers, which collect samples of product from a main body thereof. The sampler may be operated to withdraw a series of small, measured amounts of the product as it passes a sampling point, thereby to obtain a composite sample of the product.

Various types of samplers have been used to withdraw samples of product from pipes or vessels. With some samplers the product flows into an opening in a probe and is then removed, for example by being forced out of the probe by the pressure of the product in the pipe, by being gravitationally conveyed through and out of the probe, or by being collected within the probe for subsequent removal, such as by dumping. Such samplers depend on the flowability of the product into and/or out of the probe for proper operation, and are not well suited for sampling product that has a tendency to plug up the probe opening.

Another type of sampler continuously diverts a stream of product from a line or vessel, and from the diverted stream samples are removed in various ways. Attempts to withdraw small, measured quantities directly from a pipe or tank, however, have presented problems not altogether satisfactorily solved. For example, in the case of a sampler comprising a probe that has a receiving hole or slot extended directly into a pipe, the sampler often requires an orienting mechanism, and sampled product can build up in such holes and slots and either block the sampler or contaminate subsequent samples.

With some samplers discrete samples are removed from a main body of product by extending a sample receiving chamber into, and then extracting the chamber from, the body of product. Such samplers are usually characterized by a housing having a bore, with one end of the bore communicating with the interior of a product containing vessel. A plunger is in the bore and has a recess intermediate its ends. Means are provided for reciprocating the plunger in the bore to project the recess into the vessel to receive a sample of product therein, and to then retract the recess and product sample from the vessel to a sample collection point in the bore. Seals on the plunger to opposite sides of the recess maintain a seal between the one end of the bore and the sample collection point during reciprocation of the plunger.

While conventional samplers operate satisfactorily with product that is relatively fluent and of generally uniform consistency, they often are less than satisfactory for sampling fluidized product, especially when relatively large discrete particles are entrained in the product, such for example as product comprising wood pulp in which there are knots. It is difficult for such product to pass through a conventional sampler to a point of collection, and the particulate material in the product has a tendency to block openings in the sampler and otherwise interfere with movement and proper operation of the sampler.

OBJECTS OF THE INVENTION

An object of the present invention is to provide an improved sampler that is particularly adapted to sample a fluidized product in which particles of a relatively large size are entrained, for example a product such as wood pulp containing knots.

Another object is to provide such a sampler that includes a plunger assembly defining a sample chamber that is extended into and out of product to receive and convey discrete samples of the product to a collection point.

A further object is to provide such a sampler in which a seal is always maintained between product being sampled and the collection point.

Yet another object is to provide such a sampler in which the plunger assembly has a shear bearing defining a rearward side of the sample chamber, and in which the shear bearing has a circumferential groove that receives and retains fluidized product in sealing relation to a bore in which the plunger assembly is reciprocated, to seal the shear bearing and thereby the plunger assembly to the bore.

Still another object is to provide such a sampler in which the shear beating, when the plunger assembly is extended into product, slices off and returns to the product any sampled product particles that did not completely exit the collection point and extend into the bore.

A still further object is to provide such a sampler in which the shear beating acts as a transverse bearing when the plunger assembly is extended into product.

A further object is to provide such a sampler in which the plunger assembly has a cutter that cooperates with a forward end of a bore in which the plunger assembly is reciprocated to cut through product particles that would otherwise inhibit retraction of the plunger assembly into the bore.

SUMMARY OF THE INVENTION

In accordance with the present invention, a sampling apparatus comprises housing means having a bore for communicating at one end with the interior of a vessel containing fluidized product. Plunger means in the bore has a recess therein intermediate its ends, and means are provided for reciprocating the plunger means in the bore to project the recess into the vessel to receive a sample of product therein and to retract the recess from the vessel to a point in the bore. Means are at the point in the bore for receiving the sample of product in the recess, and means are provided for maintaining a seal between the one end of the bore and the point therein. The means for maintaining a seal includes first seal means on the plunger means on one side of the recess toward the one end of the bore for sealing the plunger means to the bore, and second seal means on the plunger means on an opposite side of the recess. The second seal means includes means for receiving and retaining fluidized product in sealing relation to the bore to seal the plunger means to the bore.

In a preferred embodiment of the sampling apparatus, the means for receiving the sample of product comprises a plurality of discrete passages in the housing means communicating with the bore at the point therein, the second seal means comprises shear bearing means, and the shear bearing means cooperates with the housing means around the openings to the discrete passages to slice through any fluidized product particles extending into the bore after entering, but being too large to pass through, the discrete passages. The shear beating means includes the groove medially in and extending around its outer periphery for receiving and retaining fluidized product in sealing relation to the bore to seal the outer peripheral surface of the shear bearing means, and thereby the plunger assembly, to the bore. Because the fluidized product may include particles that can interfere with retraction of the plunger means, cutter means are provided on the plunger means on the one side of the recess toward the one end of the bore, and the cutter means cooperates with the housing means at the one end of the bore, upon retraction of the plunger means from the vessel, to cut through any fluidized product particles that might otherwise interfere with retraction of the plunger means.

The foregoing and other objects, advantages and features of the invention will become apparent upon a consideration of the following detailed description, when taken in conjunction with the accompanying drawings.

DETAILED DESCRIPTION

Figure 3:
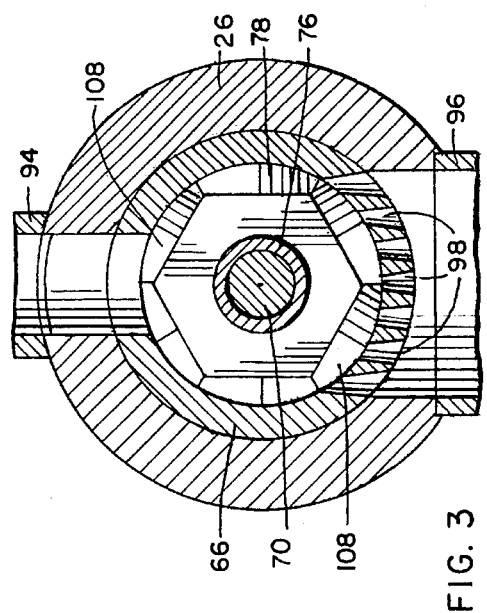
FIG. 3 is a cross sectional view taken substantially along the lines 3—3 of FIG. 2, and FIGS. 4–6 are views of the forward end of the sampler structure shown in FIG. 2, illustrating sequential stages of operation of the sampler in obtaining a sample of product from the vessel.
Figure 1:
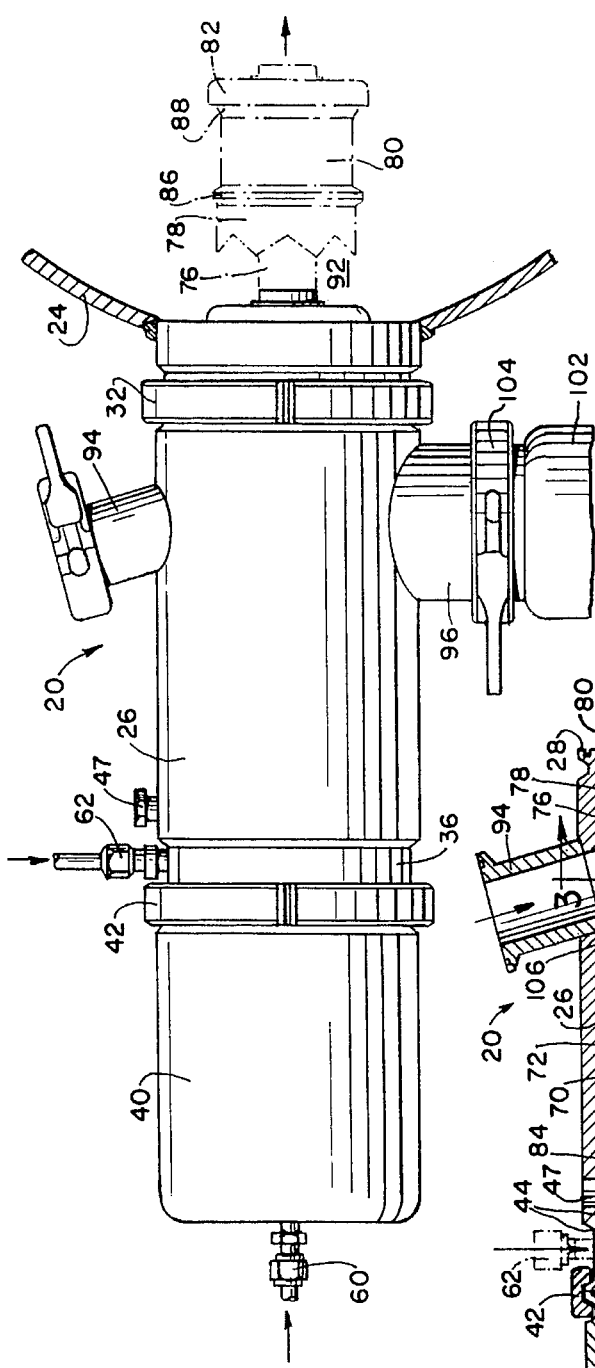
FIG. 1 is a side elevation view illustrating a sampler according to the invention, mounted on a product vessel for extension of a sample chamber into the vessel to withdraw a sample of product.

In the drawings there is indicated generally at 20 a sampler structured according to a preferred embodiment of the invention. The sampler is adapted for connection with an access line 22 to a conduit, vessel or pipe 24 in which fluidized product is conveyed, in which product may be entrained relatively large product particles. The sampler has a plunger assembly that is partially extendable into the vessel for receiving within a sample chamber a sample of the product, with the plunger then being retractable to convey the sample to a collection point in the sampler. The sampler may be cyclically actuated so that the collected product represents a composite sample of product flowing through the conduit, and seals on the plunger assembly always maintain a liquid seal between the vessel and the collection point. The sample chamber is washed clean by the product each time a sample is obtained, so that the collected samples accurately represent the product in the conduit.

The sampler 20 includes a body 26 having toward its forward end a flange 28 that connects to a flange 30 on the adaptor 22 by means of a quick release clamp 32 to mount the sampler on the adaptor, and a seal 34 establishes a fluid tight connection between the flanges. A head 36 is connected at its forward end to the rearward end of the body by a plurality of fasteners 38 (only one of which is shown). A barrel 40 is connected at its forward end with a rearward end of the head by a quick release clamp 42 that grips facing flanges on the barrel and head, seals 44 are between the body and head, and a seal 46 is between the head and barrel. Vents 47 in opposite sides of the body communicate with an interior chamber 49 at the rearward end of the body to accommodate venting, draining of leakage and flushing of the rearward interior of the body.

Motor means for operating the sampler includes the barrel 40 in which is defined a cylinder passage 48. A piston 50 is slidably sealed with the cylinder passage by a pair of seals 52, and a sleeve 54 extends forwardly from the piston through a passage 56 in the head 36 with which it is slidingly sealed by a pair of seals 58. To reciprocate the piston, an air inlet 60 communicates with the cylinder passage on a rearward side of the piston and an air inlet 62 communicates with the cylinder passage on a forward side of the piston. Pressurized air at the inlet 60 moves the piston and sleeve forwardly or rightwardly (as shown in the drawings), while introduction of air at the inlet 62 moves the piston and sleeve leftwardly or rearwardly.

The sampling portion of the sampler 20 includes the body 26 within which is a body passage 64. A carrier 66 is in the body passage and within the carrier is a cylindrical carder passage or bore 68. The sleeve 54 extends part way into the bore and a spindle 70 extends through the sleeve and between the piston 50 and the forward end of the bore. Coaxially supported by the spindle for reciprocation in the bore and forming a plunger assembly are, from left to right as seen in the drawings, an extension cap 71, an extension 72, a cylindrical shear bearing 74, a spool 76, a cutter 78, a support 80 and an end cap 82. The extension 72 is sealed to the surface of the bore 68 by a seal 84 between the extension and extension cap and annular seals 86 and 88 seal with the bore on opposite sides of the support 80. A forward end of the sleeve 54 is received in a rearward recess 90 in the extension 71 and the various components of the plunger assembly are maintained together and under axial compression between the forward end of the sleeve 54 and the cap 82. A rearwardly extending circumferential flange of the cap 82 is of a slightly greater diameter than the diameter of the bore 68 and engages the forward end of the carrier 66 to limit rearward retraction of the plunger assembly.

The remainder of the sampler comprises means for obtaining product samples. Around the spool 76 and between the shear bearing 74 and the cutter 78 is an annular recess or sample chamber 92. The sample chamber is extendible out of the bore 68 and into the product line 24 upon forward reciprocation of the plunger assembly, and upon rearward reciprocation the sample chamber with a product sample therein is retracted into the bore to a sample collection point in the bore between a fluid inlet conduit 94 and a sample outlet conduit 96. The fluid inlet conduit 94 communicates with the bore 68 at the collection point through aligned passages in the body 26 and carrier 66, and the sample outlet conduit 96 communicates with the bore at the collection point through a plurality of discrete outlet passages 98 in the carrier and a single passage in the body. The outlet passages advantageously are formed through the carrier by electro-discharge machining and are tapered to increase in diameter in the outward direction from the bore to facilitate movement of product samples therethrough. An annular flange 100 at the lower end of the sample outlet conduit facilitates convenient attachment of the sample outlet conduit to a sample processing system (not shown) or to a sample receiving container 102 by means of a quick release clamp 104.

In operation of the sampler 20, the plunger assembly is reciprocated in the passage or bore 68 to project the sample chamber or recess 92 into the vessel 24 to receive a sample of fluidized product therein, and to then retract the plunger assembly to withdraw the sample chamber from the vessel and back into the bore to the collection point at the sample outlet passages 98. Conventionally, elastomer seals would be provided on the plunger assembly on opposite sides of the sample chamber to maintain a liquid seal between the collection point in the bore and the interior of the product vessel during reciprocation of the plunger assembly, a conventional sampler and such a seal arrangement being shown in U.S. Pat. No. 4,147,062, issued to the present inventor on Apr. 3, 1979, and the entirety of the teachings of which are specifically incorporated herein by reference. However, unlike known samplers, according to one feature of the present invention, such elastomer seals are not provided on the plunger assembly to both sides of the sample chamber 92. There is an elastomer seal 86 to the right of the sample chamber, but there is no such seal to the left. The reason an elastomer seal is not used just to the left of the sample chamber is because the seal would have to move back and forth across the openings to the sample outlet passages 98, and such openings, particularly when the passages are formed by electro-discharge machining, are relatively sharp and would quickly grate or erode away and destroy an elastomer seal. Therefore, instead of an elastomer seal to the left of the sample chamber, there is provided the shear bearing 74 that has a close fit to the bore 68 and in which there is an annular circumferential recess or groove 106 located generally medially in a cylindrical peripheral surface of the shear bearing. The annular groove does not, by itself, form a seal between the periphery of the shear beating and the bore. However, in operation of the sampler fluidized product enters, fills and is retained in the groove and forms a seal with the surface of the bore to thereby seal the circumferential periphery of the shear bearing, and therefore the plunger assembly, to the bore. While for the purpose of description only a single annular groove is shown, it is contemplated that more than one annular groove could be used, and that the groove need not be annular, but instead could follow a nonlinear or tortuous path around and in the cylindrical peripheral surface of the shear bearing 74.

Figure 4:
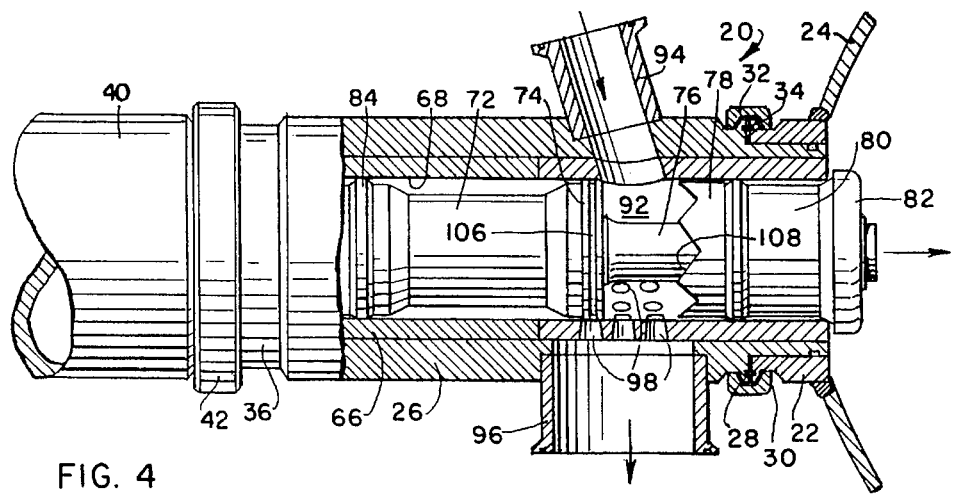
Figure 5:
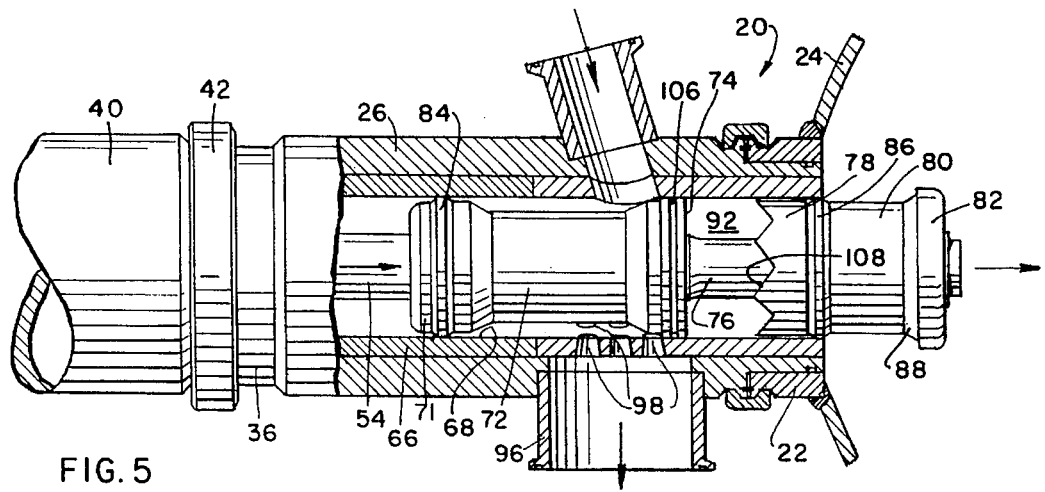
Figure 6:
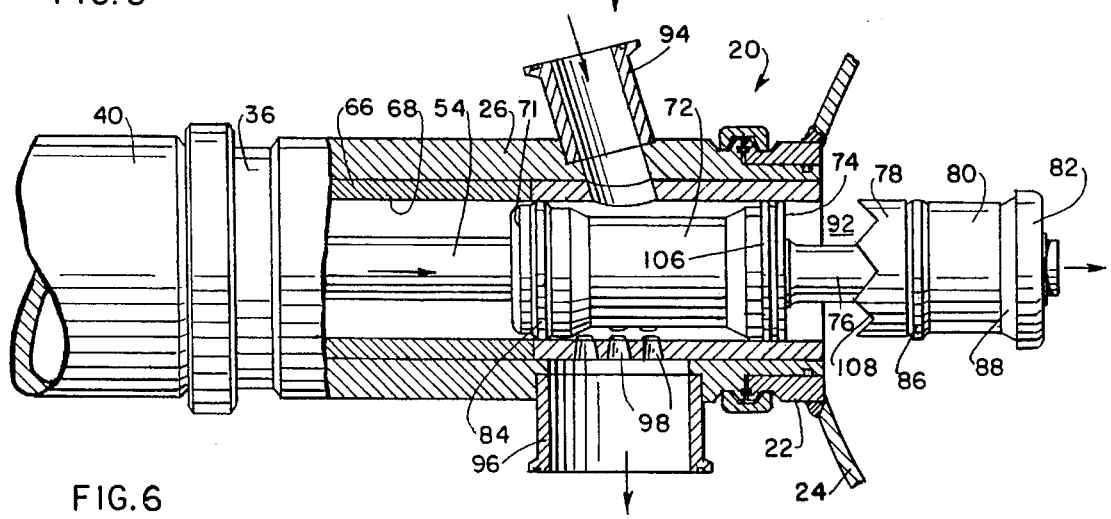

FIGS. 4–6 illustrate various positions of the plunger assembly as it is reciprocated to extract a product sample from the vessel 24. As best seen in FIG. 5, the spacing between the forward seal 86 and the rearward seal developed by the annular groove 106 of the shear beating 74, is such that a liquid seal is at all times maintained between the sample collection point in the bore 68 and the interior of the vessel. As the plunger assembly is moved forwardly, the seal formed by the shear bearing moves to a position forwardly of the fluid inlet conduct 94 and the outlet passages 98 before the seal 86 moves out of the forward end of the bore. Similarly, upon retraction of the plunger assembly the seal 86 enters and seals with the bore before the seal formed by the shear beating reaches either the fluid inlet conduct 94 or any of the outlet passages 98. In consequence, product is always sealed against flow from the vessel to either the fluid inlet conduit or the outlet passages, and only product captured in the sample chamber 92 reaches the collection point in the bore.

When the plunger assembly is extended forwardly to obtain a product sample, the shear bearing 74 moves toward, but remains within, the forward end of the bore 68. Because the sampler is particularly adapted to obtain samples of fluidized product, for example a slurry such as wood pulp in which relatively large product particles such as knots may be entrained, product flowing through the conduit 24 may exert a significant transverse force on the forward end of the plunger assembly when it is extended into the vessel. However, at this time the shear bearing is forward in the bore and advantageously acts as a transverse bearing to properly support the plunger assembly. Also, when the plunger assembly is extended, the annular sample chamber 92 is placed in the product flow and is washed clean by the product stream of any remnants of the previous sample. The arrangement prevents a buildup of product in the sample chamber, as can occur with conventional samplers which use slots or holes for collecting a sample, since the open shape of the sample chamber and its direct exposure to the stream of product prevent it from becoming clogged. The sample chamber is therefore self-cleaning of debris often encountered in product lines, which debris can include rags, filaments from fiber cloths, tough and stringy chunks of product, wood chips and knots, etc. Consequently, when the sample chamber is withdrawn into the bore, it will carry a true sample of the product.

The fluidized product stream in the vessel 24, which as mentioned may comprise wood pulp, is under positive pressure, and when the plunger assembly is extended to place the sample chamber 92 in the flow of the wood pulp in the vessel, the positive pressure tries to force the wood pulp past the shear bearing 74. This causes wood pulp to enter into, fill and be retained in the annular circumferential groove 106 in the shear bearing periphery, in sealing relation to the bore 68, and thereby causes a seal to be formed between the circumferential periphery of the shear bearing and the bore to seal the plunger assembly to the bore just rearwardly of the sample chamber. The seal formed in the annular groove prevents substantial communication between the product in the vessel and the collection point in the bore when the sample chamber is extended into the vessel.

After extension of the plunger assembly into the vessel 24, it is retracted into the bore 68 to carry a product sample in the sample chamber 92 to the collection point. Because the product is a slurry in which "debris" may be entrained, such as knots in the case of wood pulp product, the cutter 78 at the forward end of the sample chamber is provided with a sawtooth-shaped rearwardly facing cutting blade 108. The outer circumferential diameter of the cutter is such that upon retraction of the plunger assembly into the bore, the cutting blade cooperates with the front edge of the bore to slice through any knots or other material that might block or otherwise impede retraction of the plunger assembly into the bore.

Figure 2:
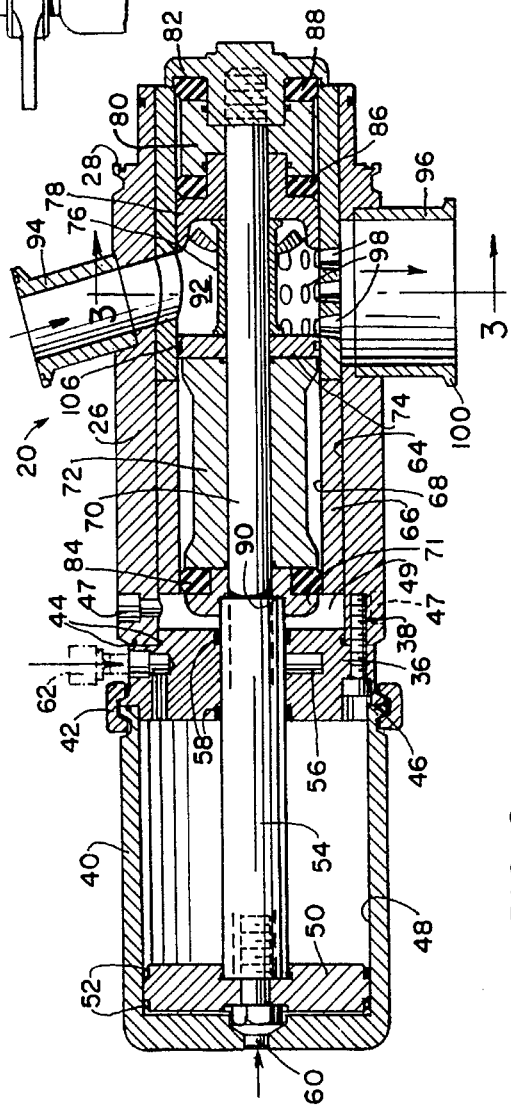
FIG. 2 is a cross sectional side elevation view of the sampler.

When the plunger assembly is fully retracted into the bore 68 it occupies the position shown in FIG. 2, where the annular sample chamber 92 is positioned at the collection point in the bore and over the sample outlet passages 98. To facilitate removal of the product sample from the sample chamber, a stream of air or other suitable fluid or liquid can be applied through the fluid inlet conduit 94 to flush the sample from the chamber and through the outlet passages. This enables substantially any type of fluidized product to readily be ejected from the sample chamber and to flow through the outlet passages and the outlet conduit 96 to the sample receiving container 102.

The sample outlet passages 98 are sized to act as a screen and thereby permit removal from the sample chamber 92 of only relatively small particles of product, which in the case of wood pulp would comprise small fibrous material, but not relatively large knots. Larger pieces of product cannot flow through the outlet passages and either remain fully in the sample chamber or become caught in the outlet passages. Because the outlet passages are tapered outwardly, any knots that cannot pass through and become caught in the outlet passages will project partially inwardly of the sample chamber and the bore 68. The shear bearing 74 is therefore formed of a relatively hard material, so that upon the next forward extension of the plunger assembly, the forward outer peripheral edge of the shear bearing will cooperate with the inner sharp edges of the outlet passages 98 to slice off any parts of those knots that are caught in the outlet passages and that extend inwardly of the bore. The severed parts of the knots or other debris are then carried forwardly in the sample chamber and are washed out of the sample chamber as the next product sample is collected therein. It can be appreciated that a conventional elastomer seal could not be used in place of the unique seal formed by the product itself, since a conventional seal would be grated away and destroyed upon being moved back and forth across the sharp openings to the outlet passages and would not be suitable for or capable of slicing off product pieces that are caught in the outlet passage and extend into the bore.

The invention therefore provides a novel sampler for fluidized products, such as those comprising a slurry. The invention provides a sampler having a unique shear bearing which utilizes the sampled product to form a seal with a bore within which the shear bearing is reciprocated; which functions as a transverse bearing when the plunger assembly is extended into the product line; and which cuts off any product pieces that may be caught in one or more relatively small outlet passages leading from a collection point in the sampler bore.

While one embodiment of the invention has been described in detail, various modifications and other embodiments thereof may be devised by one skilled in the art without departing from the spirit and scope of the invention, as defined in the appended claims.

What is claimed is:

1. A sampling apparatus, comprising housing means having a bore for communicating at one end with the interior of a vessel containing fluidized product; plunger means in said bore and having a recess therein intermediate opposite ends thereof; means for reciprocating said plunger means in said bore to project said recess into the vessel to receive a sample of the fluidized product therein and to retract said recess from the vessel to a point in said bore; means at said point in said bore for receiving the sample of the fluidized product in said recess; and means for maintaining a seal between said one end of said bore and said point therein, said means for maintaining a seal including first seal means on said plunger means on one side of said recess toward said one end of said bore for sealing said plunger means to said bore and second seal means on said plunger means on an opposite side of said recess, said second seal means including means for receiving and retaining the fluidized product in sealing relation to said bore to seal said plunger means to said bore.

2. Sampling apparatus as in claim 1, wherein said means for receiving and retaining the fluidized product in sealing relation to said bore to seal said plunger means to said bore comprises a groove around said plunger means.

3. Sampling apparatus as in claim 1, wherein said bore and said plunger means are cylindrical, said recess in said plunger means is an annular recess, and said means for receiving the sample of the fluidized product comprises a plurality of discrete passages in said housing means communicating with said bore at said point therein and through which the sample of the fluidized product flows.

4. Sampling apparatus as in claim 1, wherein said bore and said plunger means are cylindrical and said first and second seal means are circular.

5. Sampling apparatus as in claim 1, wherein said first and second seal means seal said plunger means to said bore on opposite sides of said point in said bore when said recess is at said point, said first seal means is projected out of said one end of said bore and into the vessel when said recess is projected into the vessel, and said second seal means moves toward said one end of said bore and past said point in said bore prior to projection of said first seal means out of said bore and into the vessel.

6. Sampling apparatus as in claim 1, wherein said means for reciprocating said plunger means in said bore comprises motor means coupled to said plunger means.

7. Sampling apparatus as in claim 1, wherein said second seal means has an outer peripheral surface positioned adjacent to and geometrically conforming to said bore and recess means in and around said outer peripheral surface thereby forming said means for receiving and retaining the fluidized product in sealing relation to said bore to seal said plunger means to said bore.

8. Sampling apparatus as in claim 7, wherein said plunger means and said bore are cylindrical, said second seal means peripheral surface is cylindrical and positioned adjacent to said bore, and said recess means comprises at least one groove in and extending circumferentially around said peripheral surface.

9. Sampling apparatus as in claim 8, wherein upon projection of said plunger means recess into the vessel said second seal means remains in said bore and is exposed to and contacted by the fluidized product from the vessel.

10. Sampling apparatus as in claim 1, including cutter means on said plunger means on said one side of said recess toward said one end of said bore, said cutter means cooperating with said housing means at said one end of said bore upon retraction of said plunger means from the vessel to cut through any fluidized product particles that might otherwise interfere with retraction of said plunger means.

11. Sampling apparatus as in claim 1, wherein said means for receiving the sample of product comprises a plurality of discrete passages in said housing means communicating with said bore at said point therein and through which the sample of the fluidized product flows, said second seal means comprises shear bearing means, and said shear bearing means cooperates with said housing means around openings to said discrete passages to cut through any fluidized product particles extending into said bore after entering, but being too large to pass through, said discrete passages.

12. Sampling apparatus as in claim 1, wherein the fluidized product is flowing through the vessel and past said sampling apparatus and said second seal means comprises shear bearing means, said shear bearing means being moved toward but remaining in said one end of said bore and serving the function of a transverse bearing upon said recess being projected into the vessel.

13. A sampling apparatus, comprising housing means having a bore for communicating at one end with the interior of a vessel containing fluidized product; plunger means in said bore and having a recess therein intermediate opposite ends thereof; means for reciprocating said plunger means in said bore to project said recess into the vessel to receive a sample of product therein and to retract said recess from the vessel to a point in said bore; means at said point in said bore for receiving the sample of product in said recess; and means for maintaining a seal between said one end of said bore and said point therein, said means for maintaining a seal including first seal means on said plunger means on one side of said recess toward said one end of said bore for sealing said plunger means to said bore and second seal means on said plunger means on an opposite side of said recess, said second seal means comprising shear bearing means for supporting said plunger means in said bore and for sealing said plunger means to said bore.

14. Sampling apparatus as in claim 13, wherein said shear bearing means includes means for receiving and retaining the fluidized product in sealing relation to said bore to seal said shear bearing means, and thereby said plunger means, to said bore.

15. Sampling apparatus as in claim 13, wherein said means for receiving the sample of the fluidized product comprises a plurality of discrete passages in said housing means communicating with said bore at said point therein and through which the sample of the fluidized product flows, and said shear bearing means cooperates with said housing means around openings to said discrete passages to cut through any fluidized product particles extending into said bore after entering, but being too large to pass through, said discrete passages.

16. Sampling apparatus as in claim 13, including cutter means on said plunger means on said one side of said recess toward said one end of said bore, said cutter means cooperating with said housing means at said one end of said bore upon retraction of said plunger means from the vessel into said bore to cut through any fluidized product particles that might otherwise interfere with retraction of said plunger means.

* * * * *